United States Patent [19]
Shetty

[11] Patent Number: 5,869,340
[45] Date of Patent: Feb. 9, 1999

[54] PLANT CLONES CONTAINING ELEVATED SECONDARY METABOLITE LEVELS

[75] Inventor: Kalidas Shetty, Amherst, Mass.

[73] Assignee: University of Massachusetts, Boston, Mass.

[21] Appl. No.: 771,241

[22] Filed: Dec. 20, 1996

[51] Int. Cl.$^6$ .......................... A01H 4/00; C07K 14/415; C12N 5/04

[52] U.S. Cl. ................................ 435/410; 435/4; 435/41; 435/70.1; 435/243; 530/350; 530/370; 530/379; 800/200; 800/DIG. 9

[58] Field of Search ............................. 800/200, DIG. 9; 435/41, 4, 70.1, 410, 243; 530/350, 370, 379

[56] References Cited

U.S. PATENT DOCUMENTS

| | | |
|---|---|---|
| P.P. 8,645 | 3/1994 | Sturtz . |
| P.P. 9,124 | 5/1995 | Johnson .................................. 134/359 |
| 3,915,800 | 10/1975 | Kang et al. ................................ 195/31 |
| 4,377,636 | 3/1983 | Kang et al. ............................. 435/101 |
| 5,017,397 | 5/1991 | Nguyen et al. . |
| 5,190,927 | 3/1993 | Chang et al. ............................. 514/54 |
| 5,413,928 | 5/1995 | Weathers et al. .................... 435/240.4 |
| 5,513,663 | 5/1996 | Van Leuven et al. . |

FOREIGN PATENT DOCUMENTS

PCT/US96/20741  12/1996  WIPO .

OTHER PUBLICATIONS

ATCC Bacteria and Bacteriophages, 1996 Ordering Catalog, pp. 22, 101, 103.

Schwarz, K., et al., "Evaluation of Antioxidative Constituents from Thyme," *J. Sci. Food Agric.*, 70, pp. 217–223 (1996).

Kikuzaki, H., et al., Structure of a New Antioxidative Phenolic Acid from Oregano (*Origanum vulgare* L.), *Agric. Biol. Chem.*, 53 (2), pp. 519–524 (1989).

Frankel, E., et al., "Antioxidant Activity of a Rosemary Extract . . . Carsonol, and Rosmarinic Acid, in Bulk Oil and Oil–in–Water Emulsion," *J. Agric. Food Chem.*, 44, pp. 131–135 (1996).

Jain, M., et al., "In Vitro Production of Essential Oil from Proliferating Shoots of *Rosmarinus officinalis*," *Planta Med.*, 57, pp. 122–124 (1991).

Alfano, J., et al., "Bacterial Pathogens in Plants: Life up against the Wall," *The Plant Cell*, 8, pp. 1683–1698 (1996).

Hammond–Kosack, K., et al., "Resistance Gene–Dependent Plant Defense Responses," *The Plant Cell*, 8:1773–1791 (1996).

Winterhoff, H., et al., "On the Antigonadotropoic Activity of Lithospermum and Lycopus Species and Some of their Phenolic Constituents," *Planta medica*, 54:101–106 (1988).

De–Eknamkul, W., et al., "Tyrosine Aminotransferase: The Entrypoint Enzyme of the Tyrosine–Derived Pathway in Rosmarinic Acid Biosynthesis," *Phytochemistry*, 26:1941–1946 (1987).

Bajaj et al., "Biotechnology of the Micropropagation of Medicinal and Aromatic Plants", *Biotechnology in Agriculture and Forestry*, 4:60–103 (1988).

Curtis et al., "Comparison of the Inhibitory and Lethal Effects . . . on a Food Spoilage Yeast (*Debaromyces Hansenii*)", *Food Biotechnology*, 10(1):55–73 (1996).

Eguchi et al., "Interaction of Hyperhydricity–Preventing . . . Rosmarinic Acid–Producing Clones", *Food Biotechnology*, 10(3):191–202 (1996).

Kohl et al., "Proline metabolism in N2–fixing root nodules: Energy transfer and regulation of purine synthesis", *Proc. Natl. Acad. Sci. USA*, 85:2036–2040 (1988).

Peake et al., "The Inhibitory Effect of Rosmarinic Acid on Complement Involves the C5 Convertase", *Int. J. Immunopharmac.*, 13:853–857, (1991).

Shetty et al., "Selection of High Phenolics–Containing Clones of Thyme . . . Using Pseudomonas Sp", *Journal of Agricultural and Food Chemistry*, 44:3408–3411, (1996).

Shetty et al., "Prevention of Vitrification . . . by Pseudomonas spp.", *J. Plant Physiol.*, 147:447–451 (1995).

Shetty et al., "Specific Interaction of Mucoid Strains . . . of Hyperhydricity in Tissue Culture", *J. Plant Physiol.*, 149:605–611 (1996).

Shetty et al., "Reduction of hyperhydricity . . . from Pseudomonas spp", 120:175–183, (1996).

Tada et al., "Rosmarinic Acid . . . of *Ocimum Basilicum*", *Phytochemistry*, 42:431–434, (1996).

Yang et al., "Tissue Culture–Based . . . Using Pseudomonas Strain F.", *Food Biotechnology*, 11(1):73–88, (1997).

Zheng et al., "Apple Processing Wastes As Carrier . . . Bioremediation and Plant Pathogen Control", *The Future of Biotechnology as We Approach the 21st Century*, MIT Conference, Thursday, May 30, 1996.

Lamaison et al. Pharm Acta Helv., vol. 66, No. 7, 1991, pp. 185–188.

Shetty et al. J. Plant Physiol., vol. 147, No. 3–4, Dec. 1995, pp. 289–480.

Rosales et al. Phytopathology. vol. 85, No. 9, Sep. 1995, pp. 1028–1032.

*Primary Examiner*—Jeffrey Stucker
*Assistant Examiner*—Phuong T. Bui
*Attorney, Agent, or Firm*—Fish & Richardson, P.C., P.A.

[57] ABSTRACT

A method for selecting plants and plant tissue cultures that contain elevated levels of secondary metabolites is disclosed. The method uses clonal organogenic tissue culture lines, the cultures being derived from cells of a member of the Lamiaceae family. Cultured tissue propagules are placed in contact with mucoid, non-pathogenic bacterial cells and cultured for a period of time. Those clonal lines exhibiting tolerance to the bacterial cells have elevated levels of secondary metabolites. Cultured tissue from such lines can be regenerated into plants, which are used to more efficiently produce essential oils for food and medicinal purposes.

24 Claims, 2 Drawing Sheets

PLANT CLONES CONTAINING ELEVATED SECONDARY METABOLITE LEVELS

FIELD OF THE INVENTION

This invention relates to plants that produce elevated levels of secondary metabolites and methods of selecting such plants. More particularly, the invention relates to plants of the Lamiaceae family that produce elevated levels of secondary metabolites such as rosmarinic acid, thymol, or carvacrol.

BACKGROUND OF THE INVENTION

Essential oils from herbs and spices of the Lamiaceae family increasingly are being used as antioxidants. In addition, essential oils from several herbs have antimicrobial properties. Among the secondary metabolites found in essential oils from Lamiaceae plants, rosmarinic acid ($\alpha$-O-caffeoyl-3,4-dihydroxy-phenyllactic acid) is one of the most abundant.

Among various Lamiaceae herbs and spices, oregano is an important plant widely used in South European cuisine. Essential oils obtained from oregano have antioxidant activity. Antioxidant activity was observed when essential oils from oregano were added to lard, salad dressing, or model food systems. Among the secondary metabolites found in oregano are carvacrol, thymol, and rosmarinic acid, which appear to be important for antioxidant activity. Thymol and carvacrol also have antimicrobial activity.

Essential oils from thyme (*Thymus vulgaris* L) have antioxidant properties and it is suspected that these may result from the presence of free radical scavengers in these oils. The antioxidant property of essential oils of thyme has been correlated with phenolic secondary metabolites such as thymol and carvacrol. In addition, these compounds have been shown to have bactericidal and fungicidal properties. These essential oils are sources of natural preservatives for a variety of food and medical applications.

Rosemary (*Rosmarinus officinalis*) is a member of the family Lamiaceae. The major commercial sources of rosemary are from diverse global markets; most of the processing of rosemary into extracts and the use of such extracts is carried out in developed countries. The essential oil of rosemary is presently used in flavor preparations, perfumery, and medicine. Rosemary extracts contain a large number of compounds, including carnosic acid, carnosol, and rosmarinic acid.

Oregano, thyme, rosemary, sage, holy basil, mint, and other plants in the family Lamiaceae (formerly Labiateae) are naturally cross-pollinating species and, therefore, populations are genetically heterogeneous. This heterogeneity results in significant variation in secondary metabolite content in such populations.

Current breeding and selection methods for Lamiaceae are not as well developed as methods for many other plants. Therefore, there is considerable variation in the secondary metabolite levels in essential oil extracts from such plants, even when extracts are obtained from the same source or production region.

To improve ingredient quantity and uniformity it would be useful to develop elite plant varieties with uniform genetic backgrounds. This process generally is difficult using traditional plant breeding techniques due to insufficient knowledge concerning the genetics of secondary metabolism in Lamiaceae and the high degree of heterogeneity in populations of Lamiaceae species.

SUMMARY OF THE INVENTION

The invention is based on the discovery that organogenic tissue propagated in culture can be used to select elite clones that produce elevated levels of secondary metabolites. The invention uses clonal organogenic tissue culture lines, the cultures being derived from cells of a member of the Lamiaceae family. Cultured tissue propagules are placed in contact with mucoid, non-pathogenic bacterial cells and cultured for a period of time. Those clonal lines exhibiting tolerance to the bacterial cells have elevated levels of secondary metabolites such as rosmarinic acid, thymol or carvacrol.

A method for identifying clonal lines containing elevated levels of secondary metabolites comprises the step of contacting a plurality of propagules (e.g., shoots) from at least one Lamiaceae clonal line with mucoid, non-pathogenic bacteria. The propagules are cultured (in vitro) for a time sufficient for growth to occur. The level of at least one secondary metabolite is measured in the propagules and compared to the level of the secondary metabolite in propagules of the same clonal line that have been cultured in the absence of any contact with the bacteria. The comparison is used to identify a clonal line having an elevated level of the secondary metabolite relative to the level in the untreated propagules not contacted with the bacteria. The secondary metabolite that is elevated may be thymol, carvacrol, salvianolic acid or rosmarinic acid.

The line can be initiated from species including, without limitation, *Mentha spicata, M. pulegium, M. piperita, Thymus vulgaris* L., *Origanum vulgare, Rosmarinus officinalis, Melissa officinalis, Lavandula augustifolia* or *Salvia officinalis*. The bacteria can be a species of Pseudomonas, Azotobacter, Beijerinkia or Azomonas, e.g., Pseudomonas species such as *P. mucidolens* and *P. elodea*.

The method can further comprise the step of regenerating at least one plant from the first plurality of propagules.

Also disclosed herein is a method for producing clonal lines containing elevated levels of secondary metabolites, comprising the steps of contacting propagules from a plurality of Lamiaceae clonal lines with mucoid, non-pathogenic bacteria, culturing said propagules for a time sufficient for growth to occur, and selecting at least one line that is tolerant of the contact. Propagules of the selected line contain elevated levels of at least one secondary metabolite relative to the corresponding level in propagules of the selected line cultured in the absence of contact with the bacteria. The method can further comprise the step of regenerating at least one plant from the propagules of the selected line. Such a plant has elevated levels of the secondary metabolite.

Also disclosed herein is a method for stimulating elevated levels of secondary metabolites in a Lamiaceae plant, comprising the step of contacting the plant with mucoid, non-pathogenic microbes. The microbes may comprise a Pseudomonas species or a species of *Trichoderma harzianum*.

A plant is disclosed herein, produced by contacting propagules of Lamiaceae clonal lines with mucoid, non-pathogenic bacteria, culturing said propagules for a time sufficient for growth to occur, selecting at least one line that is tolerant of the contact, and regenerating the plant from the selected line. Such a plant has elevated levels of the secondary metabolite, relative to the level in a plant regenerated from propagules of the selected line cultured in the absence of contact with the bacteria. The selection may further comprise comparing the level of the secondary metabolite in the bacteria-treated propagules to the level in propagules cultured in the absence of contact with the bacteria. The secondary metabolite that is measured can be thymol, carvacrol, rosmarinic acid or salvianolic acid.

The plant can be a species such as Mentha spicata, M. pulegium, M. piperita, Thymus vulgaris L., Origanum vulgare, Rosmarinus officinalis, Melissa officinalis, Lavandula augustifolia or Salvia officinalis. The bacteria can be a species of Pseudomonas, Azotobacter, Beijerinkia or Azomonas, e.g., Pseudomonas species such as P. mucidolens and P. elodea.

Clonal lines selected according to the invention and plants obtained from such lines can be used to efficiently produce essential oils for food and medicinal purposes. These essential oils are extracted by standard techniques.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

Figure 1:
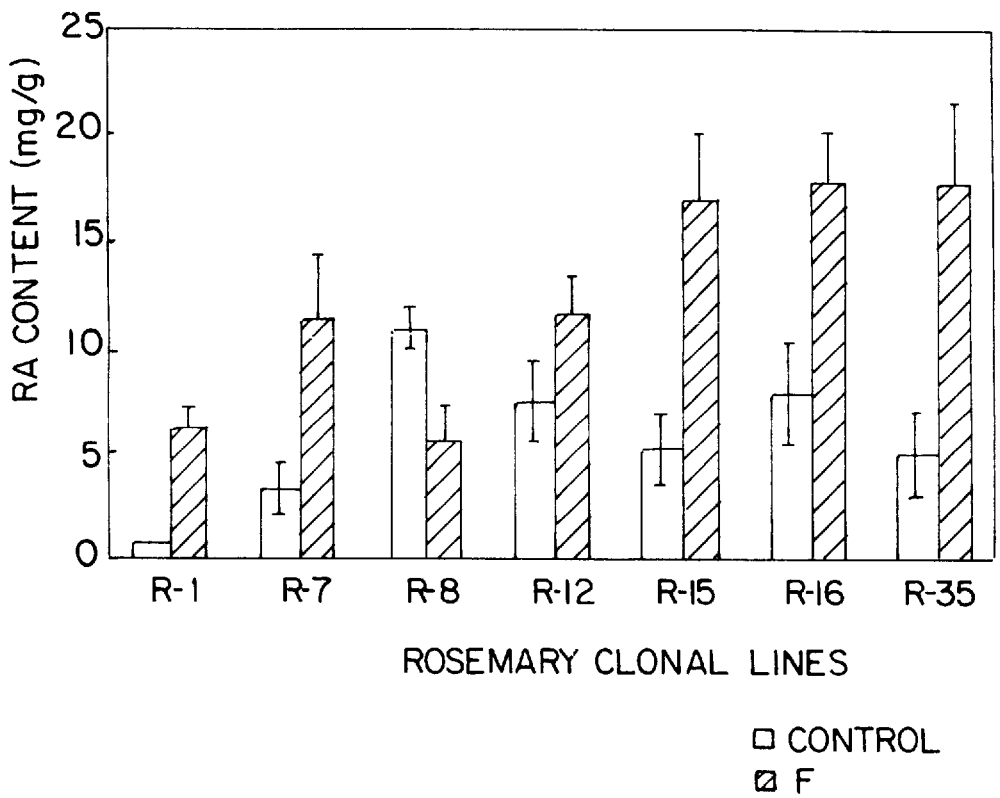
FIG. 1 is a bar graph showing the rosmarinic acid (RA) content in control and Pseudomonas-treated rosemary shoots at 25 days after inoculation. Open bars are control shoots; solid bars are shoots treated with strain F. The error bars indicate the standard deviation.

The presence of genetic heterogeneity in populations of thyme, sage, oregano, rosemary and other plants of the family Lamiaceae results in high variability in secondary metabolite content in individual plants. This heterogeneity poses problems for predictable commercial production of secondary metabolites from populations of such plants. The cost of producing medicinal and food products from such herb and spice plants is thereby increased.

A method of the invention comprises the use of organogenic tissue propagated in culture to select elite clones that produce elevated levels of secondary metabolites. These clones are selected to be tolerant of, and to grow in the presence of, mucoid, non-pathogenic bacteria. Clonal lines that produce elevated levels of secondary metabolites are not inhibited in growth in the presence of mucoid, non-pathogenic bacteria such as Pseudomonas spp., whereas growth of clonal lines not producing such elevated levels is inhibited. Therefore, there is a direct correlation between bacterial tolerance and the level of secondary metabolites in individual clonal lines. Plants regenerated from such selected populations have elevated levels of secondary metabolites. Because individuals in a clonal population are genetically identical, each selected population has a more uniform level of such secondary metabolites.

Clonal lines are generated from a species in the Lamiaceae family. Such species include, without limitation, Mentha piperita, M. arvensis, M. spicata, M. viridis, Borage officinalis, Melissa officinalis, Ocimum gratissimum, O. sanctum, O. basilicum, Salvia officinalis, Thymus vulgaris L., Origanum vulgare, Lavandula augustifolia and Rosmarinus officinalis.

Clonal lines are generated from in vitro organogenic cultures of a desired plant species. Such cultures typically are generated from seeds, axillary buds, shoot meristems or cut cotyledons of the desired plant species. A preferred organogenic culture is a shoot organogenic tissue culture. Alternatively, embryogenic callus culture can be used, generated from the same plant tissues as those used to generate organogenic cultures.

Preferably, a plurality of clonal lines are generated, each line originating from a single heterozygous plant or plant part of a single species. Clonal lines can be generated, multiplied and maintained indefinitely in tissue culture by subculturing. Each line is multiplied in culture so that a plurality of tissue propagules from each line are available for subsequent steps. Because each population is derived from a single genotype, tissue propagules in each clonal line are genetically identical.

Organogenic cultures typically are initiated on semi-solid media containing plant hormones appropriate to generate the desired type of organ. Such media typically comprise salts, vitamins, an energy source, an osmotic agent, a gelling agent, and the like. For example, shoot organogenic tissue culture can use a Murashige and Skoog (MS) media formulation supplemented with a cytokinin such as benzyladenine, kinetin, thidiazuron, zeatin, or adenine sulfate. For some species, media is supplemented with a cytokinin and an auxin, to provide an appropriate balance of hormones that promotes tissue growth and organ generation. Media formulations suitable for initiating and maintaining an organogenic culture are developed by means known to the skilled artisan, e.g., testing various amounts of different hormones to identify an appropriate cytokinin and the optimum concentration thereof.

The new method comprises contacting tissue propagules of at least one clonal line with cells of a mucoid, non-pathogenic bacterial strain. Such bacteria produce mucopolysaccharides, e.g., galactoglucans, glycosoaminoglucans and other polysaccharides that are highly viscous in concentrated form. Mucopolysaccharides produced by preferred strains have a glucose:galactose ratio of about 3:1 to about 4:1, and can be up to about 9:1.

Polysaccharides such as alginates, xanthan gums, and gellan gums are less useful in selecting and identifying clonal lines with elevated levels of at least one secondary metabolite. Therefore, bacterial strains producing such polysaccharides are less preferred.

Bacterial strains useful in the invention should also be non-pathogenic strains, e.g., strains that are considered incompatible with the species and cultivar of plant to be contacted. An incompatible strain can cause disease on other species or cultivars but does not cause disease on the cultivar to be contacted; instead the strain induces a hypersensitive response on such a cultivar. The use of compatible bacterial strains is to be avoided, because such strains will rapidly colonize and kill the plant tissue after contact between the tissue and the bacteria.

Suitable bacterial species are Gram-negative species such as Pseudomonas, Azotobacter, Beijerinkia or Azomonas. Pseudomonas strains are preferred, e.g., Pseudomonas species such as *P. mucidolens* and *P. elodea*. An illustrative embodiment of a suitable mucoid, non-pathogenic Pseudomonas strain is Pseudomonas sp. strain F, described hereinbelow. Another suitable Pseudomonas strain is strain M4. Suitable strains can be obtained, for example, from the American Type Culture Collection (ATCC), Rockville, Md. or the USDA Northern Regional Research Laboratory, Peoria, Ill.

A plurality of organogenic tissue propagules of each line are contacted with bacterial cells. Such contact can occur by, e.g., dipping tissue propagules in a bacterial suspension, touching pieces to bacterial colonies grown on solid medium, or injecting a bacterial suspension into tissue propagules. Other means of contacting bacteria and tissue propagules will be recognized by those of skill in the art. Contact is maintained for a short period of time, e.g., less than 5 minutes, preferably less than about 1 minute. Tissue preferably is rinsed afterwards with sterile distilled water.

The concentration of bacteria in a suspension is from about $10^3$/ml to about $10^7$/ml, depending on the species to be treated. For example, rosemary tissue can be contacted with higher concentrations of bacteria than thyme or oregano tissue. However, shoot tips of tissue inoculated at high concentrations can be further subcultured to reduce the inoculum load and effectively select desired lines.

Tissue propagules are cultured or incubated on semi-solid media that supports growth and proliferation of new organs, e.g., shoots. Tissue propagules and associated bacteria are incubated for a period of time in a growth room or growth chamber to allow selection to occur. Incubation conditions are adjusted to take into account the tissue and species being incubated. For example, conditions for optimum growth of thyme shoot organogenic tissue is about 23° C. and 16/8 hours day/night light cycle at a light intensity of about 2000–3000 lux.

The length of the incubation period depends upon the growth rate of the particular tissue and species under selection. For example, an incubation period of about 10 to about 60 days, preferably from about 20 to about 50 days, more preferably about 30 to about 50 days is used for thyme shoot tissue. For oregano shoot tissue, an incubation period of about 10 to about 60 days, preferably from about 20 days to about 40 days, more preferably from about 30 days to about 40 days is used.

During the incubation period, tissue propagules of clones that cannot tolerate the presence of mucoid, non-pathogenic bacteria will become necrotic and die. Such lines exhibit symptoms of hyperhydricity. Hyperhydricity or vitrification is a physiological malformation affecting clonally propagated plants in tissue culture. Such malformed tissues are enlarged, thick, translucent and brittle. This phenomenon is associated with chlorophyll deficiency, poor lignification and excessive hydration of tissues.

Tissue propagules of those clonal lines that are genetically predisposed to tolerate the presence of the mucoid bacteria will grow and survive. Such lines are not significantly inhibited by the presence of the inoculated bacteria and do not exhibit symptoms of hyperhydricity. Tissue propagules of such clonal lines produce elevated concentrations of secondary metabolites.

It is preferable to carry out a parallel control incubation using a plurality of tissue propagules from each clonal line, of like age and subculture regimen, that have not been contacted with bacteria. Such a control incubation allows more accurate quantitative of the increase in secondary metabolite concentration for bacteria-resistant clones. Such a control incubation also ensures that the necrosis observed in bacteria-sensitive clones is due to the bacteria rather than some other abiotic or biotic factor.

At the end of the incubation period, tissue propagules from clones tolerant of the bacteria are analyzed for the concentration of at least one secondary metabolite. Most such secondary metabolites in Lamiaceae are phenolic secondary metabolites and include, without limitation, rosmarinic acid, thymol, carvacrol, salvianolic acid, lithospermic acid and various flavonoids. If desired, all or a plurality of secondary metabolites can be determined, e.g., the levels of carvacrol, thymol and rosmarinic acid can be measured in oregano. The particular metabolite or metabolites chosen to be measured will, of course, depend upon the species and cultivar under selection. It is known that each species and cultivar has a particular spectrum of secondary metabolites that can be produced by that species and cultivar.

If desired, the total phenolic content can be measured to estimate secondary metabolite levels. Such a measurement is often simpler and less expensive for initial screening of a plurality of clonal lines than is a measurement of a specific secondary metabolite or metabolites. The total phenolic content of selected lines is higher, on a fresh weight basis, than the content of Pseudomonas-sensitive lines. The total phenolic content of selected lines is also often higher on a dry weight basis.

The secondary metabolite concentration in tissue exposed to Pseudomonas cells is compared to the corresponding concentration in tissue from the same clonal line that has been cultured under similar conditions but in the absence of exposure to Pseudomonas cells. Those lines in which the secondary metabolite concentration is higher, on a fresh weight or dry weight basis, in the tissue exposed to Pseudomonas are considered to be elite lines.

For some species, it is known that secondary metabolites accumulate in special organs in the plant. For these species, it may be desirable to determine the secondary metabolite level in plants regenerated from tissue propagules surviving the bacterial selection process, after such plants have developed the appropriate organ. For example, thymol analysis typically is done at later developmental stages when leaf glandular cells for thymol accumulation are more fully developed.

After selection and identification of clonal lines producing elevated levels of at least one secondary metabolite, tissue propagules of selected lines can be regenerated into plants. Regeneration is accomplished by means known in the art. Typically, tissue propagules are transferred to semi-solid media containing altered levels of plant hormones. For example, oregano shoot tissue is transferred to half-strength Murashige and Skoog (MS) medium that contains no hormones. After plantlets have formed, they are hardened off, transferred to potting soil, and allowed to mature and set seed.

Alternatively, shoots can be transferred to a regeneration medium immediately after exposure to bacteria, thus bypassing one subculture cycle.

A population of plants produced according to the invention synthesizes secondary metabolites at an elevated and preferably more uniform level than that of an unselected population. This is so because all individuals in the selected population are genetically identical. Although each plant in the population is heterozygous, substantially all of the plants have the same genotype and therefore respond in a similar manner to growth and environmental conditions by producing a similar concentration of secondary metabolites. Such plants can be propagated indefinitely from vegetative cuttings. Because the population is heterozygous, plant populations in subsequent, sexually-produced generations will not produce uniform levels of secondary metabolites.

Mucoid, non-pathogenic microbes can be used to stimulate production of secondary metabolites in clonal plant population in the field. Such microbes can be bacteria such as those used to select clonal lines or can be non-pathogenic fungi that secrete mucopolysaccharides. For example, bacterial suspensions can be sprayed on a field prior to harvest using sprayer means known in the art. As an alternative, fungal material can be applied to the plant root system, e.g., with agricultural equipment designed to apply insecticides or other chemicals. Fungal strains preferably are applied side band rather than in-furrow. Plants typically are inoculated 2–14 days before harvest, preferably 2–7 days before harvest.

Fungal strains suitable for field application include, without limitation, *Trichoderma pseudokoningii, T. harzianum, Lentinus edodes*, Pleurotus spp., Agaricus spp., or an antibiotic-producing, non-pathogenic Penicillium species. Preferred strains are saprophytic and readily colonize plants. Such strains produce a mucopolysaccharide similar to or the same as mucopolysaccharide produced by mucoid, non-pathogenic bacteria.

Tissue-culture based propagation provides a means for generating clonal lines originating from a single seed among a heterogeneous and heterozygous population of seeds. This approach can be applied to any species that is open-pollinated and, therefore, comprises genetically heterogeneous populations. Interestingly, clonal lines identified as tolerant of Pseudomonas as described herein often exhibit delayed subculture cycles and senescence even in the absence of Pseudomonas inoculation.

The use of organogenic tissues in culture to generate clonal lines, each originating from a single seed, is advantageous in that organogenic cultures do not require extensive and complicated hormone combinations to propagate such lines. The direct use of organogenic cultures also avoids the use of an intermediate callus stage when selecting desired plant clones and potential problems associated with callus cultures, such as genetic instability.

The invention will be further understood with reference to the following illustrative embodiments, which are purely exemplary and should not be taken as limiting the true scope of the present invention as described in the claims.

EXAMPLES

Example 1

Selection of Pseudomonas-Tolerant Thyme (*Thymus vulgaris* L.)

Clonal lines of thyme were generated via adventitious shoot formation from individual heterozygous seedlings. About 1000 seeds were germinated from a heterogeneous seed population (C. S. Hart Co., Chesterfield, Conn.). Nodal segments of sterile seedlings were dissected and cut in two along the axis from apex to base and then transferred basal end down to Murashige and Skoog (MS) medium containing 1 mg/L benzyladenine and 2 mM proline. The supplementation of proline did not stimulate additional shoots but did enhance the morphological uniformity among individual shoots of a clonal line. All tissue culture media and chemicals were purchased from Sigma Chemical Co., St. Louis, Mo.

About 70% of the seeds were lost due to seed-borne infection. About 7–10 adventitious shoots were induced from cut explants of each clonal line in 30–35 days. Shoots were subcultured about 4 times to generate a sufficient number of adventitious shoots for the experiment. About 100 clonal lines were developed, each clonal line originating from a different heterozygous seed.

A mucoid, non-pathogenic Pseudomonas sp. strain was isolated as a contaminant of an oregano shoot culture. This Pseudomonas sp. was termed strain F. Strain F was grown on yeast extract-mannitol medium (Difco, Inc., Detroit, Mich.) until the inoculum density was about $10^9$ colony forming units/mL. The bacterial suspension was diluted 100-fold in sterile distilled water and about 1–2 ml was dispensed into petri plates. Individual shoots of each clonal line at about 25–40 days of subculture were then inoculated by cutting the basal end of each shoot and dipping the end into the diluted bacterial suspension. Inoculated shoots were then transferred to half-strength hormone-free MS medium and incubated in a growth room at 23° C., 16/8 hours day/night. Inoculation was carried out in other experiments by contacting shoots with colonies of strain F on an agar plate. About 30–40 shoots of each clonal line were inoculated. Shoots were then used to generate a large number of clonally identical plants by inducing root formation on half-strength (hormone-free) MS medium. Control shoots of each clonal line were transferred to the same medium, but were not inoculated.

Pseudomonas tolerance was determined by visual observation at 25 days after inoculation, and each line was classified on a 4 point scale as having poor, moderate-low, moderate-high or high tolerance. Morphological variations from normal, including malformation, necrosis and chlorophyll deficiency, were evaluated among individual shoots of each clonal line under both inoculated and uninoculated conditions, using a stereo-microscope (Olympus-SZ40, Tokyo, Japan) at a magnification of 3.35×. The response of individual tissue propagules to Pseudomonas contact was similar within each line, i.e., there was little or no variation among tissue propagules within each line.

The total phenolic content was measured on leaf tissue of cultured shoots at 25 days after inoculation, using Folin-Ciocalteu reagent essentially as described in Chandler and Dodds, Plant Cell Rep. 2:105–108 (1983) and Shetty, Ph. D., Thesis, University of Idaho (1989). About 0.5 g fresh weight (FW) of leaf tissue was excised from each shoot and transferred to a tube containing 5 mL of 95% ethanol. The tissue was disrupted using a Tissue Tearor (Biospec Instruments, Racine, Wis.) and centrifuged to remove particulate matter. About 1 ml of the ethanol supernatant was mixed with an equal volume of Folin-Ciocalteu reagent (Sigma Chemical Co., St. Louis, Mo.). After incubating for 5 minutes at 25° C., 1 mL of 5% sodium carbonate was added to stabilize color development. Absorbance of the solution was measured at 725 nm using a Genesys spectrophotometer (Milton Roy, Inc., Rochester, N.Y.). A standard curve was developed using various concentrations of gallic acid in 95% ethanol. Absorbance values were converted to mg total phenolics/g FW tissue from the standard curve. Each value reported is an average of three replicate assays of three separate extracts. Representative results for 10 clonal lines are presented in Table 1.

The basal phenolics content of all uninoculated clonal lines was in the range 2.0 to 2.5 mg/g FW. The growth of inoculated shoots of clonal lines M-4, TM-4, TM-2, T-35G, M-3 was inhibited by contact with strain F. Moreover, these 5 lines had little or no increase in total phenolic content compared to uninoculated controls. Clones KM-40, T-16G, T-3 and T-13G exhibited a partial inhibition of shoot growth and a moderate increase in total phenolic content. Only clonal line T-12 had normal growth and enhanced tolerance following Pseudomonas sp. inoculation. Moreover, line T-12 had a substantial increase in total phenolic content. These results indicate that a clonal line that is tolerant of Pseudomonas sp. contains an elevated level of total phenolic secondary metabolites. Clonal line T-12, which had normal growth and an elevated total phenolic content 25 days after inoculation was characterized as an elite line.

Some control shoots were cultured on half-strength, hormone-free MS media for an additional 35 days and allowed to form roots. After 60 days in culture, leaf glandular cells on these plantlets had fully differentiated. Leaf glandular cells are a site of thymol accumulation in thyme.

These plantlets were tested for thymol content by gas chromatography with flame ionization. About 3 g of fresh leaves were clipped from 60-day old thyme plantlets using solvent-rinsed stainless steel scissors and tweezers. Leaves were transferred to a 500-mL distillation flask containing 250 mL of distilled deionized water. The flask was subsequently connected to a modified Likens-Nickerson steam co-distillation apparatus (J & W Scientific, Folsom, Calif.). After extraction with n-pentane for 2 hours, the pentane was recovered and concentrated to 1 mL under a stream of dry nitrogen. The extract was stored at −20 C. prior to analysis.

Extracts were analyzed with a Hewlett-Packard 5890 gas chromatograph. The GC oven was fitted with 30 m×0.32 mm DB-WAX fused silica capillary column (J. & W Scientific, Folsom, Calif.). The liquid phase film thickness was 0.25 $\mu$m. The GC oven was temperature programmed as follows: 40° C. (hold 8 minutes), increase at 4° C. per minutes to 240° C., hold 12 minutes. Helium carrier gas head pressure was fixed at 85 kPa with injection at 250° C. in the splitless mode. Each value reported in this study is an average of two independent analysis from two separate extractions.

Peak assignments were confirmed by GC/MS. GC/MS analyses were performed on a Hewlett-Packard 5989 GC/MS system under chromatographic conditions identical to those described for the GC/FID analysis. The GC column was directly coupled to the ion source through a heated transfer line maintained at 280° C. The mass spectrometer was operated in the electron impact mode at 70 eV.

Reference standards of thymol and carvacrol were purchased from Aldrich Chemical Company (Milwaukee, Wis.). These reference standards were used to calibrate the GC/FID and GC/MS analyses. All other chemicals were reagent grade. The results of the GC analysis are shown in Table 1.

TABLE 1

Total phenolic content, thymol content and Pseudomonas tolerance of thyme clonal lines.

| CLONE | TREATMENT | TOTAL PHENOLICS[b] (mg/g FW ± SD) | PSEUDOMONAS[a] TOLERANCE | THYMOL[b] ($\mu$g/g FW ± SD) |
|---|---|---|---|---|
| M-3 | Control | 1.5 +0.2 | | 75 ± 10 |
| | Inoculated | 2.0 +0.5 | + | |
| T-35G | Control | 1.6 +0.4 | | 55 ± 10 |
| | Inoculated | 2.2 +0.8 | + | |
| TM-4 | Control | 1.9 +0.3 | | 80 ± 10 |
| | Inoculated | 2.2 +0.1 | + | |
| M-4 | Control | 2.4 +0.2 | | 10 ± 5 |
| | Inoculated | 2.2 +0.4 | + | |
| T-13G | Control | 2.1 +0.2 | | 110 ± 20 |
| | Inoculated | 2.6 +0.4 | ++ | |
| TM-2 | Control | 2.5 +0.5 | | 110 ± 30 |
| | Inoculated | 3.0 +0.4 | + | |
| KM-40 | Control | 1.3 +0.7 | | 125 ± 20 |
| | Inoculated | 3.2 +0.5 | ++ | |
| T-3 | Control | 2.4 +0.5 | | 120 ± 15 |
| | Inoculated | 3.3 +0.5 | ++ | |
| T-16G | Control | 2.3 +0.2 | | 150 ± 15 |
| | Inoculated | 3.7 +0.6 | +++ | |
| T-12 | Control | 2.7 +1.0 | | 155 ± 15 |
| | Inoculated | 4.8 +0.3 | ++++ | |

[a]pseudomonas tolerance, determined at day 25:
+ poor;
++ moderate-low;
+++ moderate-high;
++++ high.
[b]Total phenolic content was determined on day 25; thymol content of control shoots was measured on day 60.

Clonal line T-12 had the highest thymol content (155 µg/g FW). Clonal lines T-16G, KM-40, T-3, T-2 and T-13G had thymol contents in the range 110–150 µg/g FW. Clonal lines M-3, T-35G, TM-4 and M-4 had thymol contents in the range of 0–75 µg/g FW.

Example 2

Selection of Pseudomonas-Tolerant Oregano Clonal Lines

A direct shoot organogenesis system, without an intermediate callus stage, was developed for oregano. Clonal lines of oregano were generated from individual seedlings following germination of a genetically heterogeneous seed population (C. S. Hart Co., Chesterfield, Conn.). About 1000 seeds were disinfected by immersion for 90 seconds in 70% ethanol, and 20 minutes in 2% sodium hypochlorite and subsequently 3 successive rinsings with autoclaved water for 5 minutes each and transferring to water-agar plates with 0.8% agar (Sigma Chemical Co., St. Louis, Mo.). After 30 days of germination, individual shoot apices arising from multiple areas of each seedling were excised aseptically and transferred to petri plates containing Murashige and Skoog (MS) medium (Murashige and Skoog, 1962) supplemented with 1 mg/l benzylaminopurine (BAP), 5 mM proline and 3% sucrose. All tissue culture based medium (MS-based) and vitamins were purchased from Sigma Chemical Co., St. Louis, Mo. The initial medium pH was 5.8. Each petri plate had 8 apices with each apex having two lateral leaves below it.

Petri plates containing shoot apex explants were incubated at 24° C. 16 hour light cycle with a light intensity of 40 $\mu$mol.m$^{-2}$.S$^{-1}$. After 30 days the shoot-apex explants had regenerated several more shoot apices through axillary shoot proliferation. About 7–10 new shoot apices typically were obtained from each original explant. Additional shoots were obtained from each clonal line by subculturing the original shoot explants at 30-day intervals.

Various levels of benzylaminopurine (PAP), thidiazuron (1-phenyl-3-(1,2,3-thiadizol-5-yl)urea) (TDZ) and adenine sulfate (AS) were tested for their effects on shoot organogenesis. Benzylaminopurine, thidiazuron and adenine sulfate were obtained from Sigma Chemical Co. Tissue culture optimization was carried out using oregano clone 0–1. The results of the effects on shoot organogenesis are presented in Table 2.

The results shown in Table 2 indicate that 1 mg/l PAP was a suitable level for shoot growth and formation of new adventitious shoots. Levels of PAP lower than 1 mg/l consistently induced 4–5 shoots per explant; 2.00 mg/l BAP gave about 7–10 shoots per explant but did not show much growth advantage over 1 mg/l BAP. Thidiazuron (TDZ) was ineffective in inducing shoot formation at the concentrations tested (0.25 µM–2.00 µM). At lower levels of TDZ (0.25 µM–0.75 µM), some degree of callus synthesis was observed, while at higher levels (1.00 to 2.00 µM) inhibition of explant growth without callus production was observed. Subsequent experiments used 1 mg/l BAP as a hormone supplement to the oregano culture media.

TABLE 2

Effect of Various Shoot-Inducing Hormones on Multiple Shoot Formation for Clonal Propagation of Oregano Clone 0–1

| Hormone | | Morphology | Average shoots/explant |
|---|---|---|---|
| BAP | 0.25 mg/l | shoots | 4–5 |
|  | 0.50 mg/l | shoots | 4–5 |
|  | 0.75 mg/l | shoots | 4–5 |
|  | 1.00 mg/l | shoots | 7–10 |
|  | 2.00 mg/l | shoots | 7–10 |
| TDZ | 0.25 µM | callus | none |
|  | 0.50 µM | callus | none |
|  | 0.75 µM | callus | none |
|  | 1.00 µM | growth inhibition | none |
|  | 2.00 µM | growth inhibition | none |
| AS | 2.5 mg/l | shoots | 3–4 |
|  | 5.0 mg/l | shoots | 4–5 |
|  | 7.5 mg/l | shoots | 4–5 |
|  | 10.0 mg/l | shoots | 4–5 |

Individual shoots were inoculated with strain F at 30 days after the 4th subculture. Contact of shoots with strain F was carried out as described in Example 1. Inoculated and control shoots of each line were transferred to ½ strength hormone-free Murashige and Skoog medium.

Morphological variation, including malformation, necrosis and chlorophyll deficiency, were evaluated in shoots under both inoculated and uninoculated conditions using a stereo-microscope (Olympus-SZ40, Tokyo, Japan) at a magnification of 3.35×. Results from 8 oregano clonal lines are presented below.

The subculture cycle time of each clonal line on BAP-MS medium is provided in Table 3. Clone OM-1 had a subculture cycle of about 75 days before senescence, necrosis and browning killed the tissues. On the other hand, clonal lines 0–4, 0–24 and OM-3 had a subculture cycle about 50–60 days before senescence, necrosis and browning killed the tissues. Line 0-5 had a subculture cycle of about 30–40 days.

Inoculation of Pseudomonas spp. resulted in reduced shoot growth in the first cycle ($C_0$ cycle). After 35 days of inhibited growth, all shoots were subcultured without reinoculation. All the clonal lines had rejuvenated growth during the new subculture cycle ($C_1$). When compared to uninoculated controls, senescence and necrosis of tissue of $C_1$ cycle clones carrying Pseudomonas spp. were delayed in each clonal line by 25–35 days. For example, clone 0-5 showed morphological evidence of senescence at about 30 days in the absence of inoculation, whereas senescence was delayed to about 50–60 days after inoculation with strain F ($C_1$ cycle). A similar trend was observed for all other clones. Depending on the clonal line and inoculation, subculture cycle length varied from 25 days for line 0-5 uninoculated to 90 days for OM-1 inoculated ($C_{1+n}$ cycle).

TABLE 3

Morphological Response to Pseudomonas spp. of Selected Shoot Cultures of Oregano

| Clonal Line | $C_0$ Subculture Cycle of Uninoculated Control | Tolerance to Pseudomonas spp. |
|---|---|---|
| 0-1 | 60 days | moderate (+++) |
| 0-4 | 50 days | moderate (++) |
| 0-5 | 30 days | poor (+) |

TABLE 3-continued

Morphological Response to Pseudomonas spp.
of Selected Shoot Cultures of Oregano

| Clonal Line | $C_0$ Subculture Cycle of Uninoculated Control | Tolerance to Pseudomonas spp. |
|---|---|---|
| 0-24 | 60 days | moderate (++) |
| OM-1 | 75 days | high (++++) |
| OM-3 | 60 days | moderate (+++) |
| OM-8 | 40 days | poor (+) |

A sample of inoculated and control shoots from each line were assayed for total phenolic content at 30 days after inoculation ($C_0$ cycle). About 50 mg (fresh weight) of explants were placed in 2.5 ml of 95% ethanol and held at 0° C. for 48 hours. Each sample was then homogenized with a Tissue Tearor™ (Biospec Products, Inc., Racine, Wis.) and centrifuged at 13,000×g for 5 minutes. One ml of the supernatant was removed and mixed with 1 ml of 95% ethanol and 5 ml water. To this 0.5 ml of 50% Folin-Ciocalteu reagent (Sigma Chemical, Co., St. Louis, Mo.) was added and after 5 minutes, 1 ml of 5% $Na_2CO_3$ was added to stabilize the reaction. Color was developed in 60 minutes which was measured at 725 nm using a Genesys Spectrophotometer (Milton Roy, Rochester, N.Y.). Standard curves were generated for each set of assays using various concentrations of gallic acid in 95% ethanol. Absorbance values were converted to mg total phenolic content per gm fresh weight (FW) tissue. The results are shown in Table 4.

As shown in Table 4, the total phenolic content among uninoculated clones varied between 2.07 to 3.23 mg/g FW tissue. Total phenolic content increased moderately in clonal lines 0-1, 0-4 and OM-3 in response to contact with Pseudomonas strain F. Lines 0-5 and 0-24 had an increase in total phenolic content in response to contact with Pseudomonas strain F but the increase was not statistically significant. Line OM-8 had a decrease in total phenolic content following Pseudomonas strain F inoculation.

Clonal line OM-1, on the other hand, had a large increase in total phenolic content in response to contact with strain F. Clonal line OM-1, which had the highest tolerance to Pseudomonas strain F, had an extended subculture cycle time of 75 days and the largest increase in total phenolic content. Clonal lines 0-1, 0-4, 0-24 and OM-3 had intermediate subculture cycle times and moderate Pseudomonas strain F tolerance. Clonal lines 0-5 and OM-8, which had the lowest tolerance to Pseudomonas strain F, had the shortest subculture cycle time and little or no increase in total phenolic content.

TABLE 4

Total Phenolic Content of Inoculated
Oregano Clonal Lines

| Clonal Line | Pseudomonas Treatment | Total Phenolic Content (mg/g FW ± S.D.) | |
|---|---|---|---|
| 0-1 | control | 2.07 | +0.16 |
|  | inoculated | 4.64 | +0.83 |
| 0-4 | control | 2.28 | +0.34 |
|  | inoculated | 3.85 | +0.36 |
| 0-5 | control | 2.65 | +0.76 |
|  | inoculated | 3.69 | +1.57 |
| 0-24 | control | 2.29 | +0.45 |
|  | inoculated | 3.32 | +0.70 |
| OM-1 | control | 2.29 | +0.45 |
|  | inoculated | 6.62 | +0.98 |
| OM-3 | control | 2.66 | +0.58 |
|  | inoculated | 4.21 | +1.58 |
| OM-8 | control | 3.23 | +0.52 |
|  | inoculated | 2.26 | +0.85 |

A sample of inoculated and control shoots from each line were also assayed for rosmarinic acid content. Rosmarinic acid was extracted from 50 mg of shoot tissues with 2 ml of 50% (v/v) methanol for 1 h at 55° C. After cooling the sample to room temperature, 1 ml of extract was transferred to a 16×100mm test tube and diluted by adding 3 ml of 50% (v/v) methanol. The absorbance was measured at 333 nm with Spectronic® Genesys™ 5 spectrophotometer (Spectronic Co., Rochester, N.Y.). The rosmarinic acid concentration was calculated from the absorbance at 333 nm using $\epsilon_{333}=19,000$ $\tau mol^{-1}cm^{-1}$. Total rosmarinic acid content was expressed as mg/g fresh weight of tissue.

The basal rosmarinic acid (RA) content varied among inoculated clones from 1.6 mg/g fr. wt. to 2.9 mg/g fr. wt. Clonal line OM-1 had the highest increase in RA of 2.9 mg/g/ fr. wt. 30 days following Pseudomonas inoculation. Clonal lines 0-1, 0-4 and OM-3 had increases of 1.7, 2.4 and 1.9 mg/g fr. wt., respectively. Lines 0-24, 0-5 and OM-8 had increases in RA stimulation in the range of 0.3 to 0.9 mg/g fr. wt. 30 days following Pseudomonas inoculation. There was a good correlation between Pseudomonas strain F tolerance, subculture cycles, senescence and RA levels. From the measurement of phenolics and RA following Pseudomonas inoculation, it appeared that OM-1 was a superior line, whereas 0-5 and OM-8 were inferior clonal lines.

TABLE 5

Rosmarinic Acid Content of Inoculated Oregano Clonal Lines

| Clonal Line | Pseudomonas Treatment | Rosmarinic Acid (mg/gm FW ± S.D.) | |
|---|---|---|---|
| 0-1 | control | 1.6 | +0.7 |
|  | inoculated | 3.3 | +0.2 |
| 0-4 | control | 1.6 | +0.8 |
|  | inoculated | 4.2 | +0.2 |
| 0-5 | control | 1.8 | +0.8 |
|  | inoculated | 2.7 | +0.9 |
| 0-24 | control | 2.6 | +0.1 |
|  | inoculated | 2.9 | +0.5 |
| OM-1 | control | 2.8 | +0.3 |
|  | inoculated | 5.7 | +0.8 |
| OM-3 | control | 2.7 | +0.6 |
|  | inoculated | 4.6 | +0.2 |
| OM-8 | control | 2.9 | +0.4 |
|  | inoculated | 3.1 | +0.3 |

The results from another experiment with lines 0-4 and 0-5 are shown in Table 6. Clonal line 0-4, which is able to grow after exposure to Pseudomonas strain F, has increased levels of RA at 30 and 41 days. Clonal line 0-5, which is inhibited in growth after exposure to strain F, does not have increased levels of RA.

TABLE 6

Rosmarinic Acid in
Oregano Clonal Lines 0-4 and 0-5 after
Exposure to Pseudomonas sp.

| Clonal Line | Pseudomonas Treatment | RA (mg/g FW ± SD) |
| --- | --- | --- |
| 0-4[a] | Control | 1.7 (0.1) |
|  | Inoculated | 3.9 (0.5) |
| 0-5[a] | Control | 2.8 (1.3) |
|  | Inoculated | 2.2 (0.7) |
| 0-4[b] | Control | 3.3 (0.6) |
|  | Inoculated | 7.1 (1.4) |

[a]Analyzed 30 days after exposure to pseudomonas.
[b]Analyzed 41 days after exposure to pseudomonas.

Shoot apices from clonal lines were transferred after the $C_5$ cycle to half-strength MS medium that did not contain hormones. Shoots developed roots after about 25 days. The plantlets were transferred to potting mix with vermiculite and allowed to continue development in a growth chamber at 90% humidity, 24° C. and a 16 hour day/8 hour night light cycle. Plantlets that developed into normal plants were transferred to a greenhouse. Plantlets derived from inoculated clonal lines had a higher chlorophyll content compared to the corresponding uninoculated controls and more readily adapted to greenhouse conditions than did corresponding uninoculated controls. Clonal line OM-1 adapted easily to greenhouse conditions following tissue culture-based propagation, whereas clones 0-24, 0-5 and OM-8 had to be acclimatized for extended periods under high humidity before transfer to an outdoor or greenhouse environment.

Example 3

Selection of Pseudomonas-Tolerant Rosemary Clonal Lines

Clonal lines of rosemary were generated from individual seedlings after germination. About 500 seeds from a genetically heterogeneous population were disinfected by immersion for 90 s in 70% ethanol, followed by 20 minutes in 2% sodium hypochlorite. Seeds were then rinsed 3 times with autoclaved water (5 minutes each) and transferred to water-agar plates with 0.8% agar. Seeds were allowed to germinate for 30 days at 23° C. 16/8 day/night light photoperiod.

Rosemary shoot explants from each seed contained an apical bud and two adjacent leaf pairs. These explants were induced to produce multiple shoots via adventitious shoot formation by transferring them to Murashige and Skoog (MS) medium containing 1 mg/l benzylaminopurine (BAP) to expand the number of shoots from each seed.

Two types of media were used for culturing rosemary shoots. The first medium, MSBAP, was used for shoot multiplication, maintenance, and plant regeneration of clonal lines R-7, R-8 and R-15. MSBAP contained full strength MS salts, 3% sucrose, Nitsch and Nitsch vitamins, 1 mg/l BAP at a pH of 5.8. The second medium, 1/2MS/BAP, was used for maintenance of clonal lines R-1, R-3, R-12, R-16, R-33, R-35. 1/2MSBAP contained half strength MS salts and 1.5% sucrose. Other components of 1/2MSBAP were present in the same amounts as in MSBAP. Phytogel (0.3%) was used as a gelling agent for both media. All reagents were obtained from Sigma Chemical Co., St. Louis, Mo. Medium was sterilized by autoclaving under standard conditions. Subculturing was done approximately every 60–75 days. Explants were incubated at 20° C. with 24 h light. More than 50 clonal lines were generated. Data for 7 fast growing rosemary clonal lines are shown below.

After a 60-day subculture, individual shoots of each rosemary clonal line were inoculated with Pseudomonas strain F as described in Example 1. Shoot tissue propagules were then transferred to ½ strength hormone-free MS medium containing 1.5% sucrose and cultured at 20° C. with continuous light.

The rosmarinic acid (RA) level and total phenolic content of each clonal line were measured on day 25 and day 60 after inoculation. Levels in each clonal line were compared to the corresponding levels in uninoculated tissue of the same line. Rosmarinic acid was estimated by a modified spectrophotometric method. Approximately 50 mg (fresh weight) of tissue was placed in 5 ml of 50% (v/v) methanol and incubated for 2 hours at 55° C. RA content was then determined as described in Example 2. The RA content was calculated and expressed as mg RA/g fresh weight of plant tissue ($\epsilon_{333}$=19,000 l/mol. cm).

To determine total phenolic content, approximately 50 mg (fresh weight) of tissue from each line was placed in 2.5 ml 95% ethanol. After storing samples at 0° for about 48–72 h, a Tissuemizer™ (Biospec Products, Racine, Wis.) was used to homogenize the samples. After centrifugation at 13,000×g for 10 minutes, 1 ml of supernatant was placed in a test tube to which 1 ml of 95% ethanol and 5 ml of filtered/deionized water were added. One-half ml of 50% Folin-Ciocalteu reagent (Sigma Chemical Col., St. Louis, Mo.) was added to each sample. After 5 minutes at 25° C., 1 ml of 5% $Na_2CO_3$ (Fisher Scientific Co., Fair Lawn, N.J.) was added, mixed with a vortex mixer (Barstead/Thermolyne, Dubuque, Iowa), and the reaction mixture was allowed to stand for 60 minutes in darkness. Samples were again homogenized with a vortex mixer and absorbance was measured at 725 nm. Standard curves were prepared with each assay using gallic acid in 95% ethanol. Total phenolic content was expressed as mg/g fresh weight of plant material.

Figure 2:
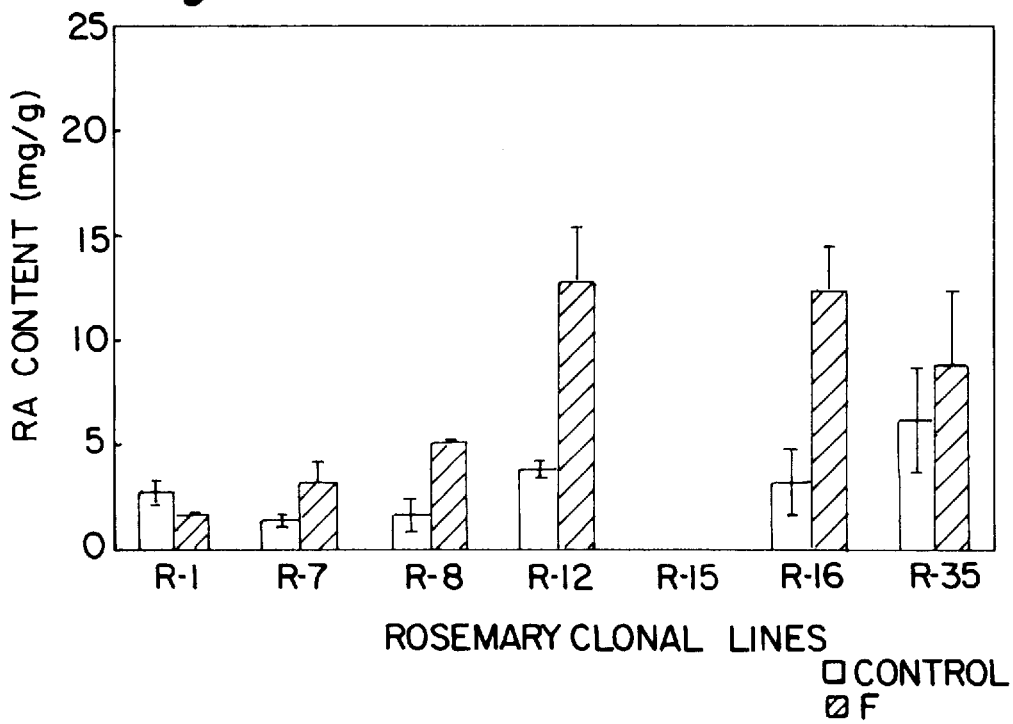
FIG. 2 is a bar graph showing the RA content in control and Pseudomonas-treated rosemary shoots at 60 days after inoculation. Open bars are control shoots; solid bars are shoots treated with strain F. The error bars indicate the standard deviation.

The level of RA in uninoculated samples of the 7 clonal lines varied from 0.77 to 11.06 mg/g fresh wt. tissue on day 25 (FIG. 1) and from 1.37 to 6.18 mg/g fresh wt. tissue on day 60 (FIG. 2).

Pseudomonas-treated shoots of lines R-7 and R-12 had similar levels of RA on day 25 (FIG. 1). By day 60, RA levels in line R-7 were reduced (FIG. 2), whereas RA levels in treated R-12 shoots remained elevated. Both lines R-7 and R-12 were tolerant of Pseudomonas content, although the tolerance of line R-12 was lower than that of R-7 (Table 7). Similar results were observed with respect to total phenolic levels in lines R-7 and R-12 (FIGS. 3 and 4).

Figure 3:
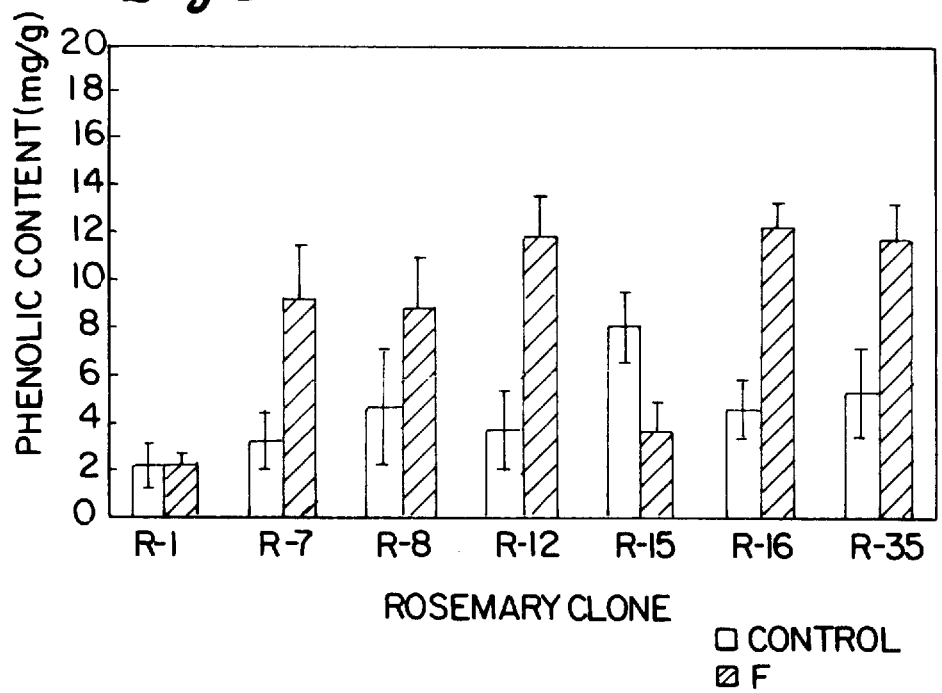
FIG. 3 is a bar graph showing the total phenolic content in control and Pseudomonas-treated rosemary shoots at 25 days after inoculation. Open bars are control shoots; solid bars are shoots treated with strain F. The error bars indicate the standard deviation.
Figure 4:
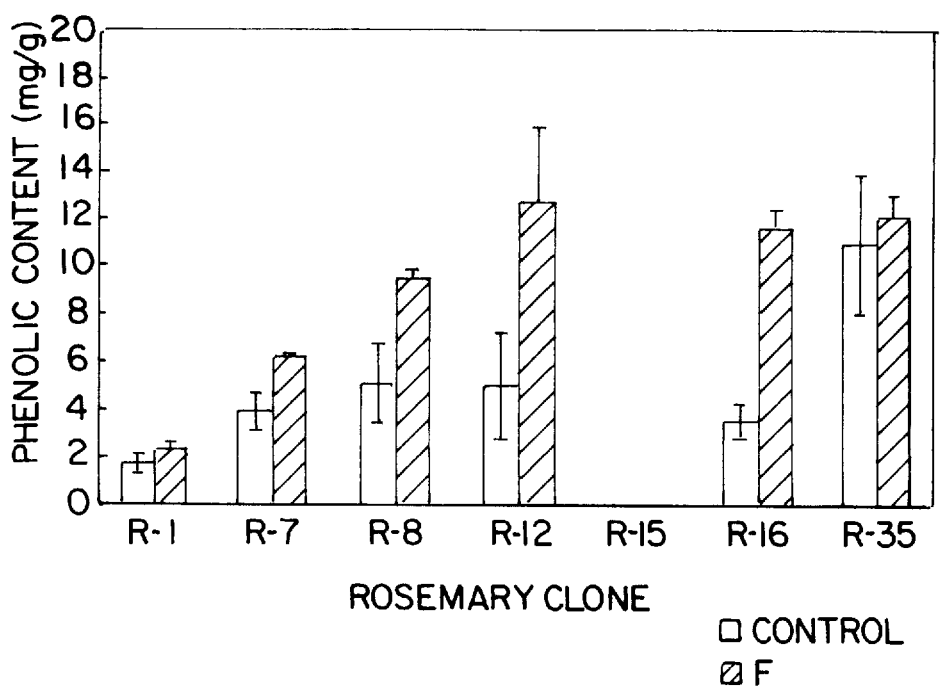
FIG. 4 is a bar graph showing the total phenolic content in control and Pseudomonas-treated rosemary shoots at 60 days after inoculation. Open bars are control shoots; solid bars are shoots treated with strain F. The error bars indicate the standard deviation.

Pseudomonas-treated shoots of lines R-16 and R-35 had elevated levels of RA stimulation on day 25 compared to untreated control shoots; levels in treated shoots had declined by day 60 (FIGS. 3 and 4). Pseudomonas-treated shoots of line R-15 had elevated levels of RA stimulation on day 25 compared to untreated control shoots (FIG. 3). However, no cultured tissue of line R-15 survived to day 60.

The total phenolic content in untreated control shoots ranged from 2.19 to 8.01 mg/g fresh wt. tissue on day 25 (FIG. 3) and from 1.75 to 10.93 mg/g fresh wt. tissue on day 60 (FIG. 4). Clonal lines R-7, R-12, R-16, and R-35 had a significant increase in phenolic content on day 25 after exposure to Pseudomonas. Line R-8 had a slight increase in total phenolic content, which was not statistically significant. Total phenolic content in line R-1 was not elevated. Total phenolic content in line R-15 was lower in Pseudomonas-treated shoots than in untreated control shoots. Total phenolic content in lines R-12 and R-16 at day 60 was high. Line R-35 had a higher total phenolic level in the treated shoots than in the untreated shoots. Interestingly, the total phenolic level of control R-35 shoots increased from day 25 to day 60.

TABLE 7

Pseudomonas tolerance of Rosemary Clones

| Clonal Lines | Pseudomonas Tolerance |
|---|---|
| R-1 | + |
| R-7 | ++++ |
| R-8 | + |
| R-12 | ++ |
| R-15 | − |
| R-16 | ++ |
| R-35 | +++ |

− inhibited
+ low
++ medium
+++ high
++++ extremely high

These data indicate that selection of rosemary shoot organogenic lines for growth in the presence of Pseudomonas is associated with elevated levels of rosmarinic acid over an extended period of time.

Example 4

Effect of Inoculation with Non-mucoid Pseudomonas

In addition to strain F described in Example 1, another mucoid, non-pathogenic Pseudomonas strain was found as a contaminant during regeneration of plantlets from in vitro shoot cultures of the 0-4 oregano clone. This strain was isolated in pure culture by standard microbiological techniques and designated as strain A. Strain A was grown on yeast extract/mannitol agar.

Strain NMA was a spontaneous, non-mucoid variant isolated from a plate containing strain A. A non-mucoid variant of strain F was obtained by chemical mutagenesis of strain F with Ethyl Methane Sulphonate, and was designated strain NMF. Classification of these microorganisms as members of the genus Pseudomonas was carried out by standard microbiological criteria.

Pure cultures of strains A, NMA, F and NMF were grown on yeast extract/mannitol agar. After 2 days incubation at 23° C., plates were stored at 2°–3° C. until needed. Oregano shoot explants were inoculated at the stem end by touching colonies on cold-stored yeast extract/mannitol agar plates. The stem end was then touched to sterile filter paper to reduce the inoculum density. The explants were then transferred to half strength MS medium (1.5% sucrose) with no hormones.

The physiological parameters that were investigated included total phenolics, chlorophyll, and water/solids content. Measurements were taken 10 and 30 days after inoculation. Samples were taken in triplicate for chlorophyll and phenolic determination while water content measurements were done in duplicate. Averages and standard deviations were determined for each treatment.

Total phenolics in oregano shoots were determined as described in Example 2.

Chlorophylls a, b, and total chlorophyll content were estimated by a spectrophotometric method. Approximately 50 mg (fresh mass) of explants were placed in 3 mL of 100% methanol in 5 mL vials, the vials were covered and incubated at 23° C. for 2 hours in darkness. Each sample was mixed and centrifuged at 6000 rpm for 5 minutes. Each sample was mixed, the methanol fraction was decanted, and the absorbance was measured at 650 nm and 665 nm. Chlorophylls were expressed as micrograms per milliliter of methanol ($\mu$g/mL) as follows:

Chlorophyll a $=16.5 \times A_{665} - 8.3 \times A_{650}$

Chlorophyll b $=33.8 \times A_{650} - 12.5 \times A_{665}$

Total Chlorophyll $=25.8 \times A_{650} + 4.0 \times A_{665}$ where $A_{650}$ and $A_{665}$ are absorbance values at 650 and 665 nm. The chlorophyll levels were then converted to micrograms of chlorophyll per gram of tissue by the formula: ($\mu$g chlorophyll/mL methanol)$\times$3 mL methanol)/(g FW tissue).

Samples of fresh tissue (about 150 mg) were placed in pre-weighed aluminum pans and allowed to dry for 24 hours at 55° C. in an oven. Pans were weighed after 24 hours and 36 hours to confirm weight stabilization. Water content of the original tissue was estimated and expressed on a 100 mg wet weight basis as follows: [(wet wt.−dry wt.)/(wet wt.)]$\times$100 Solids content on a 100 mg wet weight basis were determined as follows: (dry wt./wet wt.)$\times$100

Clonal lines 0-1 and 0-4 responded similarly to mucoid Pseudomonas strains (Tables 8 and 9). Shoots of both clones had a significantly higher total phenolic content after exposure for 10 or 30 days to mucoid strains A and F than did the untreated control shoots.

Exposure to non-mucoid strain NMF did not result in a significant increase in total phenolic content compared to the control at days 10 and 30 (Tables 8 and 9). Exposure to non-mucoid strain NMA resulted in an increase in total phenolic content for both lines at day 10. Line 0-1 also had increased total phenolic content after exposure to strain NMA at day 30, whereas the total phenolic content of line 0-4 was not significantly different from the control at day 30. The results presented here indicate that a sustained increase in total phenolic content on a fresh weight basis is associated with tolerance of mucoid, non-pathogenic strains of Pseudomonas spp.

TABLE 8

Comparison of average total phenolic content in oregano clone 0-1 after exposure to Pseudomonas strains A, F, NMA, and NMF.

| | Total Phenolics mg/g tissue (fresh mass) | |
|---|---|---|
| Treatment | Day 10 | Day 30 |
| Control | 2.7 (0.2) | 2.5 (0.2) |
| A | 4.2 (0.3)* | 3.8 (0.7)* |
| F | 5.1 (0.6)* | 3.8 (0.4)* |
| NMA | 3.5 (0.4)* | 3.4 (0.5)* |
| NMF | 3.4 (0.5) | 3.1 (0.1) |

*Mean is statistically higher than control (alpha < 0.1), student's t-test). Standard deviation in parentheses.

TABLE 9

Comparison of average total phenolic content in oregano clone 0-4 after exposure to Pseudomonas strains A, F, NMA, and NMF

| Treatment | Total Phenolics mg/g tissue (fresh mass) | |
| --- | --- | --- |
| | Day 10 | Day 30 |
| Control | 2.5 (0.2) | 2.8 (0.1) |
| A | 3.8 (0.7)* | 5.3 (1.1)* |
| F | 3.8 (0.4)* | 4.6 (0.6)* |
| NMA | 3.4 (0.5)* | 2.4 (0.3) |
| NMF | 3.1 (1.1) | 3.0 (0.4) |

*Mean is significantly higher than control (alpha <0.1, student's t-test). Standard deviation in parenthesis.

Example 5

Effect of a Mucopolysaccharide Preparation on Oregano Shoot Tissue

Mucoid strain F of Example 1 was grown at 25° C. for 48–60 hours. Bacterial cells from 80 ml of broth were separated by centrifugation for 30 minutes at 15,000 rpm. Supernatants from multiple 80 ml flasks were combined and recentrifuged as a larger volume (250 ml) to further remove cells and debris. Three volumes of ice-cold 95% ethanol were added to the supernatant to precipitate extracellular mucoid component (EMC). The ethanol solution was stored at −70° C. for 12 hours to increase EMC recovery. The EMC precipitate was recovered by centrifugation at 15,000 rpm for 20 minutes. The EMC pellet was washed thrice with 95% ethanol and once with absolute ethanol. The washed pellet was dried under vacuum and resuspended in a minimum amount of distilled water, forming a sticky gel.

A portion of the EMC preparation was freeze dried and stored at −20° C. The freeze dried EMC was thawed and resuspended in sterile distilled water at concentrations in the range of 0–400 mg/ml. Reducing sugars were determined by phenolic-sulfuric acid hydrolysis. For comparison, several monosaccharides (glucose, fucose, glucuronic acid and galactose), sucrose and xanthan gum were analyzed in parallel at concentrations of 0–400 mg/µl.

Freeze-dried EMC samples (10–15 mg per sample) were acid hydrolyzed by two methods. In the first method, the sample was hydrolysed with 1M $H_2SO_4$ for 1.5 hour sat 100° C. and derivitized to alditol acetates/peracetates. In the second method, the sample was hydrolysed with 2M trifluoroacetic acid (TFA) for 1 hours at 120° C. and sililated. Each of the derivitized hydrolysates was analyzed by gas chromatography-mass spectrometry using a Hewlett Packard, 5989 GC-MS system. The GC column oven was fitted with a 30 m×0.25 mm (i.d.) HP5 fused silica capillary column (Hewlett Packard, Avondale, Pa.) which was directly coupled to the ion source through a heated transfer line maintained at 280° C. The mass spectrometer was operated in the electron impact mode at 70 eV. A series of pure monosaccharides were analyzed concurrently. Results of the analysis are provided in Table 10.

Sugar analysis of the EMC preparation was carried out according to the method of DuBois, M. et al., Anal. Chem., 38:350–356 (1956). Standard curves of various known sugars were prepared by the same method and compared to the results of the EMC preparation. EMC aligned most closely with galactose and glucose (FIG. 1).

Protein content of the EMC was determined by the Bradford dye-binding method. The results showed that no protein was present in the EMC preparation.

TABLE 10

Monosaccharide composition of the extracellular mucoid component of Pseudomonas strain F

| Sample TD | Method of hydrolysis | Monosaccharides detected (% of total) | |
| --- | --- | --- | --- |
| | | Glucose | Galactose |
| A | $H_2SO_4$ | 87.1 | 12.9 |
| A-replicate 1 | $H_2SO_4$ | 88.2 | 11.8 |
| A-replicate 2 | TFA | 88.4 | 11.6 |
| B | $H_2SO_4$ | 85.9 | 14.1 |
| C | $H_2SO_4$ | 79.2 | 20.8 |

In total, three separate samples were analyzed and one sample, A, was done in triplicate with two modes of acid hydrolysis.

The results of the GC/MS analysis of EMC hydrolysate showed that EMC was a polysaccharide with glucose and galactose in a ratio of about 9:1 to about 8:2 (Table 10). Analysis was confirmed by several repeats using two types of derivitization (sililation and acetate derivatives) and two types of acid hydrolysis (sulfuric acid and trifluoroacetic acid).

About 2–3 g of purified EMC was mixed with water at a concentration of 10 mg/ml and sterilized by autoclaving. Plugs (about 25 mg) of the sterilized EMC-water gel were placed into wells (2.5 cm$^3$) cut into semi-solid half-strength MS medium without hormones. The concentration of EMC in each well on a weight/volume basis was approximately the same as that of the agar used in the MS medium. One shoot of line 0-1 was placed on top of each EMC plug. For comparison, other shoots of oregano clonal line 0-1 were contacted with strain F as described in Example 1 and cultured on hormone-free half-strength MS medium. Control shoots were dipped in sterile water and directly transferred to half-strength, MS hormone-free medium. Each treatment had 8 shoots/plate and 4 plates/treatment. Results similar to those discussed below were obtained when oregano shoots were cultured on MS medium containing benzyladenine.

Streomicroscopic observations of shoots after 30 days on EMC-containing media indicated that leaves of EMC-treated shoots were dark green, opaque and had epidermal hairs which are characteristic of normal leaves. The untreated control leaves were light green, translucent and devoid of epidermal hairs.

Total phenolic content, chlorophyll and water content were determined 30 days after inoculation. Total phenolic content was determined as described in Example 2.

Chlorophyll a, chlorophyll b and total chlorophyll content were estimated as described in Example 4. Water and solids content was determined as described in Example 4. The results are shown in Table 11.

TABLE 11

Comparison of average water content, chlorophyll and total phenolic content in oregano shoots of clone 0-1.

| Treatment | Water Content (mg $H_2O$/ 100 mg tissue) | Phenolics (mg/g FW tissue) | chlorophyll ($\mu$g/g FW Tissue) | | |
|---|---|---|---|---|---|
| | | | a | b | Total |
| Control | 88.4 (0.3) | 2.8 (0.5) | 412.7 (25.7) | 138.3 (9.2) | 555.9 (35.2) |
| Pseudomonas | 81.6 (0.8) | 4.2 (0.8) | 701.0 (19.9) | 234.1 (7.4) | 943.4 (27.4) |
| EMC | 83.6 (0.4) | 2.5 (0.5) | 803.6 (75.4) | 272.1 (26.8) | 1085.3 (103.1) |

Standard deviation in parentheses.
Measurements made at day 30 after inoculation.

As shown in Table 11, the chlorophyll content of EMC-treated and Pseudomonas-treated shoots was significantly higher than that of untreated control shoots, expressed on fresh weight basis.

The results of the total phenolic content analysis indicated that shoots exposed to strain F had a significantly higher total phenolic content than did untreated control shoots when expressed on fresh weight basis. No significant difference in total phenolic content was observed between untreated control and EMC-treated shoots (Table 11).

The water content of untreated control and Pseudomonas-treated shoots was significantly different (88.4% vs. 81.6%, Table 11). The EMC-treated shoots had a water content of 83.6%, which was more similar to the content Pseudomonas-treated shoots than to untreated shoots.

The chlorophyll and total phenolic content was also calculated on a dry weight basis and are shown in Table 12. There was no significant difference in total phenolic content between control and Pseudomonas-treated shoots when expressed on a dry weight basis. By comparison, EMC-treated shoots had significantly reduced levels of phenolics.

On a dry weight basis, chlorophyll a and total chlorophyll levels were significantly higher in EMC-treated shoots compared to control and Pseudomonas inoculated shoots. Chlorophyll b was significantly higher in Pseudomonas inoculated and EMC-treated shoots compared to control shoots.

TABLE 12

Chlorophyll, total phenolic content and solids content on a dry weight (DW) basis in control, Pseudomonas-treated and EMC-treated oregano shoots of clone 0–1.

| Treatment | mg solids in 100 mg tissue | Phenolics ($\mu$g/mg DW) | Chlorophyll ($\mu$g/g DW) | | |
|---|---|---|---|---|---|
| | | | a | b | Total |
| Control | 11.6 ± 0.3 | 24.1 ± 4.3 | 3.5 ± 0.2 | 1.2 ± 0.1 | 4.8 ± 0.3 |
| Pseudomonas | 18.4 ± 0.8 | 22.8 ± 4.3 | 3.8 ± 0.1 | 2.0 ± 0 | 5.1 ± 0.1 |
| EMC | 16.4 ± 0.4 | 15.2 ± 3.0 | 4.9 ± 0.4 | 1.7 ± 0.2 | 5.9 ± 0.6 |

Measurements were made 30 days after treatment.

Exposure of oregano shoots to the EMC preparation did not result in increased levels of total phenolics on a fresh weight basis; total phenolic content was decreased on a dry weight basis. In contrast, exposure to strain F resulted in a phenolic content similar to the control on a dry weight basis and significantly higher than the control on a fresh weight basis.

The ability of shoots to regenerate roots and to develop normal plants was tested. EMC-treated, Pseudomonas-treated and control shoots were cultured on half-strength MS hormone-free medium and the ability to form roots was evaluated. Rooted plantlets were transferred to vermiculite medium and covered with a transparent plastic film to prevent humidity loss. Dilute (one-eighth strength) MS basal salts were added every 5 days. After 15 days the plastic cover was removed and the humidity of the enclosed microenvironment was allowed to equilibrate to growth chamber. After 7 days the number and percentage of explants that survived the change in humidity was determined. There were 8 explants per replicate with 4 replicates for each treatment. A total of 32 explants were used for each treatment with 8 explants/replicate (plate).

TABLE 13

Regeneration of Plants from Control, EMC-treated and Pseudomonas-treated Shoots of Clonal Line 0-1.

| Treatment | Hyperhydrated[a] (%) | Normal Plants[b] (%) | Root Formation[c] |
|---|---|---|---|
| Control | 94 + 4 | 44 + 5 | ++ |
| Pseudomonas | 0 + 0 | 81 + 4 | + |
| EMC | 25 + 5 | 66 + 2 | ++ |

[a]Percentage of shoots exhibiting hyperhydricity at the initiation of the experiment.
[b]Percentage of surviving plantlets after transfer to greenhouse
[c]Root formation:
++ = high.
+ = low.

The regeneration studies (Table 13) indicated that the Pseudomonas-treated shoots adapted most effectively to sudden changes in environmental conditions. EMC-treated shoots were intermediate between Pseudomonas-treated and untreated control treatments in adaptation effectiveness (Table 13). The enhanced adaptation efficiency of Pseudomonas-treated shoots was not related to rooting stimulation, which was low for Pseudomonas-treated shoots.

Example 6

Effect of Inoculation in a Field Environment

About 100 regenerated plants of oregano clone OM-1 from Example 2 are removed from the greenhouse and planted outdoors in a field during the summer. Plants are fertilized weekly, but are not irrigated. At 7 days before flower emergence, each plant is inoculated with about 2.5 gm of dried hyphae and spores of mucoid, non-pathogenic *Trichoderma harzianum* in a dried apple pomace carrier. Half of the plants are inoculated by making a circular slit in the soil at the drip line to a depth of about 10–20 cm and sprinkling the dried fungal material into the slit. The fungal material is then watered in. The remaining control plants are treated by making a circular slit as above but without adding fungal inoculum.

After 7 days, leaf tissue from fungal-treated and control plants is harvested and analyzed for total phenolic content and RA content as described in Example 2. The results show that fungal-treated plant tissue has at least 2-fold more total phenolics and RA than control tissue on a fresh weight and on a dry weight basis.

Other Embodiments

It is to be understood that while the invention has been described in conjunction with the Detailed Description thereof, that the foregoing description is intended to illustrate and not limit the scope of the invention, which is defined by the scope of the appended claims. Other aspects, advantages, and modifications are within the scope of the following claims.

What is claimed is:

1. A method for selecting a Lamiaceae clonal plant line, said method comprising:
   a) contacting propagules from a plurality of Lamiaceae clonal lines with mucoid, non-pathogenic bacteria;
   b) culturing said propagules for a time sufficient for growth of said propagules to occur; and
   c) selecting at least one line that is tolerant of said contact, said tolerance indicated by a lack of hyperhydricity in said propagules, said propagules of said selected line containing an elevated level of a secondary metabolite relative to the corresponding level in proagules of a clonal line that is not tolerant of contact with said bacteria.

2. The method of claim 1, further comprising the step of:
   (d) regenerating at least one plant from said contacted proagules of said selected line.

3. The method of claim 1, wherein said selecting step further comprises comparing the level of said secondary metabolite in a first plurality of propagules of said selected clonal line cultured in the presence of said bacteria to the level of said secondary metabolite in a second plurality of propagules of said selected clonal line cultured in the absence of any contact with said bacteria.

4. The method of claim 1, wherein said secondary metabolite is rosmarinic acid.

5. The method of claim 1, wherein said selected line is from the species *Origanum vulgare*.

6. The method of claim 5, wherein said secondary metabolite is rosmarinic acid.

7. The method of claim 1, wherein said bacteria comprise a species of Pseudomonas.

8. The method of claim 1, wherein said bacteria comprise a species of Beijerinkia.

9. The method of claim 1, wherein said bacteria comprise a species of Azotobacter.

10. The method of claim 1, wherein said line is from the species *Mentha spicata*.

11. The method of claim 10, wherein said secondary metabolite is rosmarinic acid.

12. The method of claim 1, wherein said line is from the species *Thymus vulgaris* L.

13. The method of claim 12, wherein said secondary metabolite is thymol or carvacrol.

14. The method of claim 1, wherein said line is from the species *Rosmarinus officinalis*.

15. The method of claim 14, wherein said secondary metabolite is rosmarinic acid.

16. The method of claim 1, wherein said line is from the species *Melissa officinalis*.

17. The method of claim 16, wherein said secondary metabolite is rosmarinic acid.

18. The method of claim 1, wherein said line is from the species *Lavandula augustifolia*.

19. The method of claim 18, wherein said secondary metabolite is rosmarinic acid.

20. The method of claim 1, wherein said line is from the species *Salvia officinalis*.

21. The method of claim 20, wherein said secondary metabolite is rosmarinic acid.

22. The method of claim 1, wherein said line is from the species *Ocimum basilicum*.

23. The method of claim 22, wherein said secondary metabolite is rosmarinic acid.

24. The method of claim 1, further comprising the step of:
   (d) regenerating at least one plant from propagules of said selected plant line cultured in the absence of said contact with said bacteria, said at least one plant having an elevated level of said secondary metabolite.

* * * * *